United States Patent [19]

Yamada et al.

[11] Patent Number: 5,095,135

[45] Date of Patent: Mar. 10, 1992

[54] PROCESS FOR THE PREPARATION OF HIGH-PURITY NAPHTHALENECARBOXYLIC ACID ESTERS

[75] Inventors: Teruaki Yamada; Kazuhiko Maeda; Ryohei Minami; Yukio Nagao; Kazuki Sugiura, all of Ibaraki, Japan

[73] Assignee: Sumikin Chemical Co., Ltd., Tokyo, Japan

[21] Appl. No.: 680,502

[22] Filed: Apr. 4, 1991

[30] Foreign Application Priority Data

Apr. 5, 1990 [JP] Japan .................................. 90737
Apr. 5, 1990 [JP] Japan .................................. 90738
Jun. 20, 1990 [JP] Japan ................................ 161900

[51] Int. Cl.$^5$ ........................................... C07C 67/48
[52] U.S. Cl. ................................. 560/100; 560/77; 560/78; 562/414; 562/416
[58] Field of Search ................ 560/100, 77, 78; 562/414, 416

[56] References Cited

U.S. PATENT DOCUMENTS

| | | | |
|---|---|---|---|
| 3,55,945 | 2/1971 | Malmbog et al. ................... | 560/77 |
| 2,963,508 | 12/1960 | Barker et al. ....................... | 562/416 |
| 3,091,636 | 5/1963 | Benson ................................ | 562/416 |
| 3,092,658 | 7/1963 | Baldwin et al. ..................... | 562/416 |
| 3,119,860 | 1/1964 | Kalfadelis et al. .................. | 562/416 |
| 3,546,274 | 12/1970 | Barkowski et al. ................. | 560/77 |
| 3,674,845 | 7/1972 | Reni et al. .......................... | 562/416 |
| 4,048,021 | 9/1977 | Takamoto et al. .................. | 560/78 |
| 4,291,058 | 9/1981 | Suchy ................................. | 560/100 |
| 4,886,901 | 12/1989 | Holzhauer et al. ................. | 560/78 |

*Primary Examiner*—Bruce Gray
*Attorney, Agent, or Firm*—Burns, Doane, Swecker & Mathis

[57] ABSTRACT

A process for the preparation of naphthalenecarboxylic acid esters in which a substituted naphthalene is oxidized with molecular oxygen in the presence of a heavy metal-based catalyst in a solvent comprising a lower aliphatic monocarboxylic acid to form a naphthalenecarboxylic acid and the resulting acid is then esterified. The esterified product is purified by washing, recrystallization, and distillation in that order. Heavy metals are recovered as carbonates from filtrates and washings obtained by seeparation of crude acid and ester products and by washing thereof.

20 Claims, 1 Drawing Sheet

PROCESS FOR THE PREPARATION OF HIGH-PURITY NAPHTHALENECARBOXYLIC ACID ESTERS

BACKGROUND OF THE INVENTION

This invention relates to a process for the preparation of high-purity naphthalenecarboxylic acid esters in which a substituted naphthalene is oxidized with molecular oxygen in the presence of a heavy metal-based catalyst in a solvent comprising a lower aliphatic monocarboxylic acid to form a naphthalenecarboxylic acid (hereinafter abbreviated a NCA) and the NCA is then esterified to form an NCA ester.

Among NCA's, the monocarboxylic acid or naphthoic acid is useful in the production of photographic chemicals and dyestuffs. Naphthalene-dicarboxylic acids, and particularly naphthalene-2,6-dicarboxylic acid are useful in the production of various polyesters including polyethylene naphthalates and polyamides, which in turn are used in the manufacture of films and fibers having improved heat resistance, mechanical strength, and dimensional stability. Naphthalene-tricarboxylic acids and naphthalene-tetracarboxylic acids are promising as starting materials in the production of high-performance resins.

Various methods have been proposed for the preparation of NCA. A method which is widely used in the commercial production of NCA comprises an oxidation of an alkyl- or acyl-substituted naphthalene with molecular oxygen in the presence of a heavy metal-based catalyst in a solvent comprising a lower aliphatic monocarboxylic acid such as acetic acid.

The use of a catalyst comprising at least one heavy metal selected from cobalt and manganese and bromine in the above-mentioned method is disclosed in Japanese Patent Publication Nos. 48-43893(1973), 56-21017(1981), and 59-13495(1984), and Japanese Patent Application Kokai Nos. 49-42654(1974), 60-89445(1985), 60-89446(1985), 61-140540(1986), 61-246144(1986), and 63-104943(1988). Addition of an alkali metal to such a catalyst is proposed in Japanese Patent Application Kokai Nos. 61-246143(1986), 62-120343(1987), 62-120343(1987), 63-66150(1988), and 1-121240(1989).

The use of a catalyst comprising cobalt and nickel or cobalt and cerium as heavy metals and bromine is described in Japanese Patent Application Kokai Nos. 62-212343(1987) and 62-212344(1987).

NCA is frequently used in the form of its alkyl ester. Esterification of NCA is usually performed by reacting NCA with an alkyl alcohol in the presence of an esterification catalyst such as an acid including a Lewis acid. For example, it is proposed in Japanese Patent Publication No. 49-174(1974) that NCA is esterified with methyl alcohol in the presence of a catalyst selected from sulfuric acid, hydrogen chloride, hydrochloric acid, and organic sulfonic acids under pressure.

A crude ester product obtained by esterification of NCA is usually tinged with yellowish brown due to contamination with impurities. When such a crude ester product is used in the preparation of a polymer, the resulting polymer is undesirably colored and its quality is also degraded. Therefore, it is necessary to purify the crude ester product before use.

Various purification methods of crude NCA esters have been proposed. For example, recrystallization from hot methanol is described in Japanese Patent Application Kokai Nos. 50-84467(1975) and 50-111056(1975), while purification by distillation is described in Japanese Patent Application Kokai Nos. 57-35697(1982) and 58-29291(1983). Japanese Patent Application Kokai No. 50-116461(1975) discloses purification of a crude NCA ester by distillation followed by recrystallization. Similarly, Japanese Patent Application Kokai No. 117847/1989 discloses that a crude NCA ester is washed with methanol, distilled in vacuo, and finally recrystallized from hot methanol.

In order to prepare a high-purity NCA ester inexpensively on a commercial scale, it is important that the heavy metal catalyst used in the preparation of NCA be recovered and reused repeatedly.

Japanese Patent Publication No. 46-14339(1971) and Japanese Patent Application Kokai No. 47-34088(1972) disclose the preparation of terephthalic acid by liquid-phase oxidation of p-xylene in the presence of a heavy metal catalyst comprising cobalt and manganese. After terephthalic acid is collected from the reaction mixture by filtration, the filtrate is distilled to recover the solvent and the residue is treated so as to recover the heavy metals present therein as carbonates.

Japanese Patent Application Kokai No. 62-212345(1987) discloses a continuous process for the preparation of 2,6-naphthalene-dicarboxylic acid (2,6-NDCA) by oxidation of 2,6-diisopropylnaphthalene (2,6-DIPN) or its oxidation intermediate with molecular oxygen in the presence of a catalyst comprising cobalt, manganese, and bromine. The crude 2,6-NDCA crystals formed are separated and contacted with an aqueous mineral acid solution to dissolve out the heavy metal catalyst present thereon, and the resulting mineral acid solution from which 2,6-NDCA crystals have been separated is treated with an alkali metal carbonate or bicarbonate to recover the catalytic heavy metals as carbonates or bicarbonates.

Japanese Patent Application Kokai No. 1-121237(1989) discloses the purification of crude crystals of an aromatic carboxylic acid by washing with water or recrystallization and treating the washings or mother liquor of recrystallization with a carbonate ion-forming compound to precipitate heavy metals as carbonates.

Although various purification methods of NCA esters are known as described above, there is a need to prepare a high-purity, colorless NCA ester product efficiently and economically while recovering catalytic heavy metals for reuse.

SUMMARY OF THE INVENTION

It is an object of the present invention to provide a process for preparing a high-purity NCA ester efficiently and economically.

A further object of the invention is to provide a process capable of preparing a high-purity, colorless NCA esters while recovering catalytic heavy metals used in the formation of NCA for reuse.

The present invention is a process for preparing a high-purity NCA ester comprising the steps of (a) oxidizing a substituted naphthalene with molecular oxygen in the presence of a heavy metal catalyst, an alkali metal compound, and a bromide in a solvent which comprises a lower aliphatic monocarboxylic acid to form an NCA, (b) separating the oxidation product into a crude NCA and a filtrate, (c) washing the crude NCA with at least one of water, an acid, and an aqueous acid solution to give a washed crude NCA, (d) esterifying the washed crude NCA in the presence of an esterification catalyst in an alkyl alcohol, (e) separating the esterification product into a crude NCA ester and a filtrate, (f) washing the crude NCA ester with at least one of water, an aqueous acid solution, and an alkyl alcohol to give a washed crude NCA ester, (g) recrystallizing the washed crude NCA ester from an organic solvent to give a recrystallized NCA ester and (h) distilling the recrystallized NCA ester to give a high-purity NCA ester, wherein either one of the washing steps (c) and (f) may be eliminated.

Preferably the process further comprises the steps of (i) treating the filtrates obtained in separating steps (b) and (e) and the washings obtained in washing steps (c) and (f) with a carbonate ion-forming compound in an amount sufficient to precipitate the heavy metals present therein as carbonates, and (j) recovering the precipitated heavy metal carbonates for reuse as an oxidation catalyst in step (a). The process may further comprise the step of (k) washing the precipitates of heavy metal carbonates recovered in step (j) with at least one organic solvent selected from alkyl alcohols and ketones.

The process may be carried out in a continuous, batchwise, or semicontinuous manner.

According to the present invention, a substantial part of the heavy metals used in the oxidation reaction can be recovered easily as carbonates and reused without an appreciable decrease in catalytic activity.

DETAILED DESCRIPTION OF THE PREFERRED EMBODIMENTS

Figure 1:
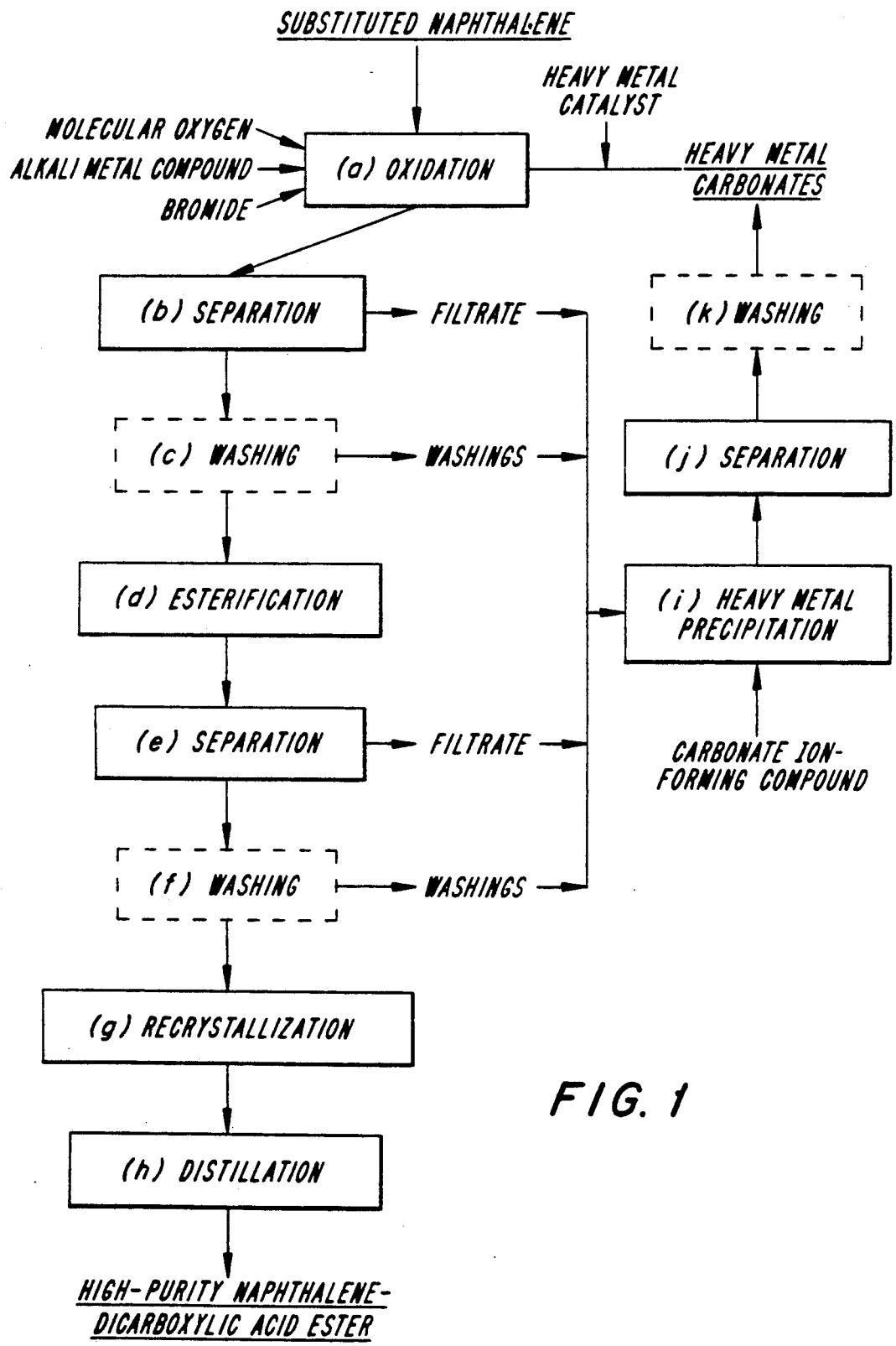
FIG. 1 is a flow chart of the process of the present invention.

The process of the present invention is carried out in the sequence shown in FIG. 1.

The substituted naphthalene useful in the process of the present invention as a starting material includes any naphthalene compound having at least one substituent selected from alkyl groups such as methyl, ethyl, and isopropyl, acyl groups such as acetyl and formyl, and oxidation intermediates of these groups. A particularly preferred substituted naphthalene is a di-substituted naphthalene having two substituents selected from methyl, ethyl, and isopropyl.

The starting substituted naphthalene is oxidized with molecular oxygen in the presence of a heavy metal catalyst, an alkali metal compound, and a bromide in a solvent which comprises a lower aliphatic monocarboxylic acid to form an NCA.

The lower aliphatic monocarboxylic acid which is used as a solvent in the oxidation stage includes acetic acid, propionic acid, butyric acid, and mixtures thereof. Acetic acid is preferred. The solvent may be comprised solely of the monocarboxylic acid or it may be mixed with another solvent which is preferably selected from those solvents having good stability for oxidation such as water and halogenated hydrocarbons, e.g., chlorobenzene and bromobenzene.

The source of molecular oxygen used in the oxidation may be air, pure oxygen, or a mixed gas of oxygen and an inert gas. Preferably air is used as the source of molecular oxygen.

The heavy metal oxidation catalyst consists of one or more compounds of heavy metals selected from cobalt, manganese, cerium, nickel, copper, iron, zinc, and the like which are soluble in the solvent used. Lower carboxylic acid salts such as acetates of these heavy metals are particularly suitable as catalysts.

The alkali metal compound can be selected from, for example, carbonates, bicarbonates, acetates, and bromides of sodium and potassium. The bromide may be an organic or inorganic compound and can be selected from hydrogen bromide, methyl bromide, bromoacetic acid, potassium bromide, sodium bromide, cobalt bromide, and manganese bromide. The alkali metal compound and bromide promote the catalytic activity of the heavy metal catalyst.

The oxidation reaction may be performed under conditions commonly employed in the prior art. Usually the reaction temperature is in the range of from 20° to 250° C. and preferably from 100° to 200° C., while the oxygen partial pressure in the reaction system is in the range of from 0.2 to 20 kg/cm$^2$-G and preferably from 3 to 15 kg/cm$^2$-G.

When the starting material is a substituted naphthalene having an ethyl or isopropyl group as a substituent, such a substituent tends to convert into a polymerizable unsaturated functional group such as vinyl or isopropenyl due to its high reactivity. As a result, the formation of polymeric by-products may occur in the oxidation reaction and it undesirably decreases the yield of the desired NCA and causes deactivation of the catalyst. Furthermore, in some cases, it is necessary to employ a certain treatment so as to remove polymeric by-products prior to the heavy metal recovery step. In order to minimize the formation of polymeric by-products in the oxidation reaction when it is performed continuously, it is preferred that the starting substituted naphthalene and the oxidation catalyst be separately fed into an oxidation reactor so as to avoid contact of these two materials before reaction.

After cooling of the oxidation reaction product, crude NCA crystals which precipitate out due to the low solubility of NCA in the reaction solvent are collected by filtration to separate them from a filtrate.

The filtration may be performed using any conventional filter such as a filter press or a centrifugal filter.

Since the crude NCA crystals contain heavy metal impurities originating from the heavy metal catalysts, they are washed with at least one of water, an acid, and an aqueous acid solution to give a washed crude NCA. Examples of the acid useful in the washing step are sulfuric acid, hydrochloric acid, nitric acid, and acetic acid. Dilute aqueous solutions of these acids can be used, too. The washing may be performed at room temperature or at an elevated temperature. Repeated washing may be employed, if desired, but it is not necessary in most cases.

The washing removes most of the heavy metal impurities present in the crude NCA into the washing solution and heavy metal-containing washings are obtained.

The filtrate separated from the crude NCA and the washings obtained by washing the crude NCA contain heavy metals, so they are treated as described below in order to recover the heavy metals.

The washed crude NCA is then subjected to esterification to form an NCA ester. The esterification may be performed in the presence of a conventional esterification catalyst in an alkyl alcohol in a conventional manner.

Examples of useful esterification catalysts include acids such as sulfuric acid, hydrochloric acid, phosphoric acid, and p-toluenesulfonic acid, tetraisopropyl titanate, and vanadium sulfate.

The alkyl alcohol used in the esterification may be at least one of methyl alcohol, ethyl alcohol, propyl alcohols, and butyl alcohols. Preferably methyl alcohol or ethyl alcohol is used.

The conditions for the esterification reaction are not critical but it is preferable that the temperature at the end of the esterification be no higher than 160° C.

After cooling of the esterification product, crude NCA ester crystals which precipitate out due to the low solubility of the ester in an alkyl alcohol at room temperature are collected by filtration to separate them from a filtrate.

Since the crude NCA ester crystals still contain a slight amount of heavy metal impurities originating from the heavy metal catalyst used in the oxidation stage, they are washed with at least one of water, an aqueous acid solution, and alkyl alcohol to give a washed crude NCA ester. The washing can be performed in the same manner as the washing of crude NCA. For the washing of the crude NCA ester, solutions of the above-described acids which can be used for the washing of crude NCA, or the above-described alkyl alcohols usable for the esterification of NCA may be used.

It is not always necessary to wash both the crude NCA and crude NCA ester in the above-mentioned manner. Thus, one of the washing steps of NCA and NCA esters may be eliminated and catalytic heavy metals can still be recovered with a satisfactorily high yield, and a high-purity, colorless NCA ester product can be obtained after the distillation step. However, in general, the results are further improved when both the crude NCA and crude NCA ester are washed.

The filtrate separated from the crude NCA ester and the washings obtained by washing the crude NCA ester contain heavy metals, and they are treated as described below in order to recover the heavy metals.

The washed crude NCA ester is then recrystallized from a suitable organic solvent to give a recrystallized NCA ester, which is finally distilled to give a high-purity NCA ester product.

The recrystallization can effectively remove heavy metal residues and part of the oxidation intermediate such as acetylnaphthoic acid and esterification by-products which may be present in the washed crude NCA ester as impurities. It is difficult to remove other impurities such as esterified oxidation intermediates, metallic compounds, esterification intermediates such as half esters, and bromides by recrystallization. As a result, if the washed crude NCA ester is purified merely by recrystallization as taught in Japanese Patent Application Kokai Nos. 50-84467(1975) and 50-111056 (1975), the resulting recrystallized NCA ester does not have a satisfactorily high purity and it is tinged with a yellowish brown color. Therefore, its quality is inadequate for use in the production of a polymer.

If the washed crude NCA ester is purified by distillation and subsequent recrystallization as taught in Japanese Patent Application Kokai Nos. 50-116461(1975) and 1-117847(1989), the heavy metals remaining in the NCA ester and concentrated at the bottom of the distillation column cause degradation of the ester, thereby decreasing the yield and quality of the NCA ester product. Furthermore, the bromide and esterification catalyst remaining in the washed NCA ester may corrode the distillation equipment. In addition, more complicated distillation equipment must be employed to remove a residual lower-boiling point by-product such as a trimellitic acid ester by distillation.

Accordingly, in order to efficiently obtain a colorless, high-purity NCA ester product which is substantially free of oxidation intermediates and their esters, esterification intermediates, metallic contaminants, and bromides, it is critical that the washed crude NCA ester be purified by recrystallization and distillation in that order.

The organic solvent which can be used for recrystallization of the washed crude NCA ester includes alkyl and aralkyl alcohols such as methyl alcohol, ethyl alcohol, and benzyl alcohol; alkylbenzenes such as toluene, xylene, and trimethylbenzene; aliphatic hydrocarbons such as hexane and heptane; and tetrahydrofuran, pyridine, dimethylacetamide, dimethylsulfoxide, dimethylformamide, chloroform, acetone, and ligroin.

The distillation conditions of the recrystallized NCA ester are not critical. It is preferable to perform the distillation at a reduced pressure so as to prevent thermal decomposition of the NCA ester which leads to deterioration in the yield and quality of the high-purity NCA ester product. In order to improve the efficiency of separation from impurities, it is also preferable to employ rectification, rather than simple distillation, using a distillation column having a large number of theoretical plates and a refluxing means.

The recrystallization and subsequent distillation of the NCA ester are preferably performed under conditions which satisfy the following inequality:

$$(B/A) + 0.4s + 2.9r > 14 \qquad (1)$$

where
A: weight of NCA ester to be recrystallized (grams),
B: weight of recrystallization solvent (grams),
s: number of theoretical plates of distillation column, and
r: reflux ratio.

When the conditions for recrystallization and subsequent distillation satisfy the above inequality (1), the resulting purified NCA ester product will have high purity and be free from coloration. Preferred conditions are as follows:
solvent ratio (B/A): at least 3,
number of theoretical plates (s): at least 5,
reflux ratio (r): at least 0.5.
More preferably, the ratio B/A is at least 8, s is at least 10, and r is at least 1.

According to the process of the invention, the heavy metal catalyst used in the oxidation stage is recovered from the filtrates separated from the crude NCA and crude NCA ester and the washings collected in the steps of washing the crude NCA and the crude NCA ester. For this purpose, these solutions (filtrates and washings) are treated with a carbonate ion-forming compound so as to precipitate heavy metals present therein as carbonates and the precipitates are collected. Although the solutions may be treated separately, it is preferable to treat the combined solutions.

In some cases, all the solutions need not be treated as above. For example, if the washings obtained by washing the crude NCA ester do not contain an appreciable amount of heavy metals, such washings may not be treated.

Although the filtrates may be treated directly, it is preferable that they be initially distilled to recover the solvents for reuse and the residues be treated with the carbonate ion-forming compound. This is particularly desirable in the case of the filtrate separated from the crude NCA, which contains a large amount of the aliphatic monocarboxylic acid used as a solvent in the oxidation. If such a filtrate is directly treated, not only can the relatively expensive monocarboxylic acid not be reused, but also it is necessary to add a large amount of an alkali before the treatment in order to neutralize the acid, and this causes the formation of a large amount of carboxylate salt which must be disposed of.

Similarly, when an aqueous solution of a volatile acid such as acetic acid or an alkyl alcohol is used in the washing steps, the resulting washings may be distilled to recover the acid or alcohol prior to treatment with a carbonate ion-forming compound. Alternatively, the washings may be concentrated prior to treatment.

When one or more of the filtrates and washings are distilled, the residues may be combined and dissolved in water or a dilute mineral acid solution and the resulting solution may be treated with a carbonate ion-forming compound.

The carbonate ion-forming compound used in the treatment may be any compound which is soluble in the solution to be treated and which liberates carbonate ions therein. Examples of useful carbonate ion-forming compounds are sodium carbonate, potassium carbonate, ammonium carbonate, sodium bicarbonate, and potassium bicarbonate. One or more of these compounds may be added to the solution to be treated in at least a stoichiometric amount required to react with the heavy metals present in the solution.

By reacting with the carbonate ion-forming compound, the heavy metals are converted into their carbonates, which are insoluble and precipitate out. Therefore, the heavy metals can be separated and recovered readily by filtration.

Preferably the treatment with the carbonate ion-forming compound is performed at a pH of 7.5 or higher and a temperature of 50° C. or higher. For this purpose, the pH of the solution after the addition of the carbonate ion-forming compound is adjusted to 7.5 or higher and the solution is heated at 50° C. or higher and more preferably at 60° C. or higher during or after the addition of the carbonate ion-forming compound. Under such conditions, the particle size of the precipitates increases. As a result, the precipitates have good filterability and can be separated by filtration in a shorter period and the recovery of heavy metals is improved.

When an alkali metal carbonate is used as a carbonate ion-forming compound, the pH of the solution can be adjusted by varying the amount of the alkali metal carbonate added. Alternatively, the pH of the solution can be adjusted by addition of an alkali such as sodium hydroxide or potassium hydroxide. The heating period depends on the pH of the solution and the heating temperature and it is usually between about 10 minutes and about 1 hour and preferably between about 30 minutes and about 1 hour.

It is preferred to wash the separated heavy metal-containing precipitates with at least one organic solvent selected from alkyl alcohols and ketones. The washing serves not only to remove organic impurities such as intermediates and polymeric by-products from the precipitates but also to reduce the moisture content of the precipitates so as to form a semi-dry state, thereby significantly facilitating the handling of the precipitates.

Examples of useful alcohol include those described above with respect to the esterification step, and examples of useful ketones are acetone and methyl ethyl ketone.

The heavy metals thus recovered from the filtrates and washings in the form of their carbonates can be recycled to the oxidation stage and reused as a catalyst either as such or after they are converted into acetates or similar salts. When the recovered heavy metal carbonates are added to the oxidation reaction as such, they react with the aliphatic monocarboxylic acid, e.g., acetic acid, used as a solvent and are converted into their carboxylate salts, e.g., acetates.

In accordance with the present invention, at least one of the crude NCA and crude NCA ester is washed to remove mainly water-soluble inorganic impurities and organic by-products. The washed crude NCA ester is purified by recrystallization to remove most of the residual organic impurities. However, it is difficult to remove some impurities, e.g., half esters and organic bromides formed as by-products by recrystallization. These impurities including colored contaminants can be effectively removed by subsequent distillation and it is possible to produce a high-purity, colorless NCA ester having a purity on the order of 99.5% or higher and preferably 99.9% or higher with a satisfactorily high yield.

Furthermore, a substantial part of the heavy metal catalyst used in the oxidation is recovered for reuse. It was confirmed that the recovered catalyst is active and can be reused repeatedly without a significant decrease in catalytic activity. As a whole, the process of the present invention can be advantageously employed in the commercial production of an NCA ester since it is possible to produce a high-purity NCA ester suitable for use in the production of a polymer efficiently and at a low cost.

The following examples are presented as specific illustrations of the claimed invention. It should be understood, however, that the invention is not limited to the specific details set forth.

In the examples the contents of heavy metals and potassium were determined by inductively coupled plasma emission spectrochemical analysis, the bromine content was determined by ion chromatography, and the purity of NCA and NCA ester was determined by gas chromatography and liquid chromatography.

EXAMPLE 1

A titanium autoclave was charged with a heavy metal catalyst consisting of 109.6 g of cobalt acetate tetrahydrate, 107.8 g of manganese acetate tetrahydrate, and 147.5 g of cerium acetate monohydrate, 157.1 g of potassium bromide and 129.6 g of potassium acetate both as promoters, and 2300 g of acetic acid as a solvent. While the resulting solution was pressurized to 30 kg/cm$^2$ with air and stirred at 200° C., 627.0 g of 2,6-diisopropylnaphthalene (2,6-DIPN) was blown through the solution over 4 hours together with excess air and thereafter only air was blown for 1 hour to complete the oxidation reaction.

After the reaction mixture was cooled, the precipitates were collected by filtration and dried to give 930.2 g of crude 2,6-naphthalenedicarboxylic acid (2,6-NDCA). The purity of the crude 2,6-NDCA was about 64% and the yield thereof was 93.9 mol % based on the amount of 2,6-DIPN.

The crude 2,6-NDCA was esterified without washing. A Hastelloy autoclave was charged with 900 g of the crude NDCA along with 9000 g of methyl alcohol and 180 g of 98% sulfuric acid and the resulting solution was allowed to react for 4 hours at 120° C. After cooling, the reaction mixture was filtered to separate the esterified product which precipitated out from the filtrate to give 740 g of crude 2,6-NDCA dimethyl ester (2,6-NDCA ester).

The crude 2,6-NDCA ester was washed with 7400 ml of water by stirring at room temperature for 30 minutes. After washing, the insolubles were separated by filtration and dried to give 665 g of pale yellow washed crude 2,6-NDCA ester, which had a purity of 98%.

The washed crude 2,6-NDCA ester (600 g) was recrystallized from 6000 g of methyl alcohol in a glass-lined autoclave by heating at 120° C. for 0.5 hours followed by cooling to 30° C. The precipitates were collected by filtration to give 596 g of recrystallized 2,6-NDCA ester.

The recrystallized 2,6-NDCA ester (550 g) was then distilled in a vacuum distillation column at a reflux ratio of 2. The number of theoretical plates of the column was 20. Under these conditions, the value for $[(B/A)+0.4s+2.9r]$ was calculated to be 23.8, which satisfied inequality (1). The distillate from which a 0.5% initial boiling cut and a 5% bottom were removed was collected as the desired 2,6-NDCA ester product.

The product had a purity of 2,6-NDCA dimethyl ester of 99.9% plus and it contained 5 ppm of 2,6-NDCA monomethyl ester, at most 20 ppm of ethyl naphthoate isomers, 0.5 ppm of bromine, and 0.3 ppm of sulfur. It had a Hazen number of 20, indicating that it was substantially colorless.

The 2,6-NDCA ester product was copolymerized with ethylene glycol and a colorless polyethylene-2,6-naphthalate was formed.

The filtrate from which the crude 2,6-NDCA formed by the oxidation reaction had been separated was evaporated so as to remove acetic acid and water, leaving a solid residue containing heavy metals. Similarly, the filtrate from which the crude 2,6-NDCA ester had been separated was also evaporated so as to remove methyl alcohol, water, and low-boiling point organic by-products, leaving a heavy metal-containing slurry. The remaining solid residue and the slurry were combined and dissolved in 10 volumes of water. The resulting solution was filtered to remove insolubles and combined with the washings obtained in washing of the crude 2,6-NDCA ester. To the combined solution an aqueous 15% sodium carbonate solution was added in an amount sufficient to increase the pH to 8 and heated for 30 minutes at 60° C. with stirring.

After cooling the solution, the reddish gray precipitates which separated out were collected by filtration and dried to give 221 g of reddish gray solids. The solids had a good filterability and the filtration was completed in a short period on the order of 3 minutes. When the solids were treated with methyl alcohol, their appearance changed from clay-like to powdery, thereby improving the handling properties. Upon the analysis of the solids, it was found that 97.0% of cobalt, 96.5% of manganese, and 98.2% of cerium based on the amounts of heavy metals used in the oxidation reaction were recovered.

When these recovered heavy metals in the form of carbonates were used as a catalyst to perform oxidation of 2,6-DIPN under the same conditions as above, the yield of the resulting crude 2,6-NDCA was 93.1 mol %. Thus, no substantial loss in yield of 2,6-NDCA was observed when the recovered heavy metal compounds were used as an oxidation catalyst.

EXAMPLE 2

A crude 2,6-NDCA (680 g) obtained by oxidation of 2,6-DIPN in the same manner as described in Example 1 was washed with a mixture of 6800 g of water and 208 g of sulfuric acid at 20° C. by stirring for 1 hour. The slurry was filtered to collect a washed crude 2,6-NDCA.

The washed crude 2,6-NDCA was esterified with methyl alcohol. A Hastelloy autoclave was charged with 433 g of the washed crude 2,6-NDCA, 4330 g of methyl alcohol, and 204 g of 98% sulfuric acid and the mixture was allowed to react for 4 hours at 120° C. At the end of the esterification, the reaction mixture was filtered and 469 g of crude 2,6-NDCA dimethyl ester having a purity of 98% was collected.

The crude 2,6-NDCA ester was purified without washing by recrystallization and subsequent distillation in the same manner as described in Example 1 to give purified 2,6-NDCA product.

The product was of a quality similar to that of Example 1. It had a purity of 2,6-NDCA dimethyl ester of 99.9% plus and it contained 6 ppm of 2,6-NDCA monomethyl ester, at most 20 ppm of naphthoate esters, 0.5 ppm of bromine, and 0.3 ppm of sulfur.

The filtrates obtained from the oxidation and esterification were distilled in the same manner as described in Example 1 and the residues were combined and dissolved in 20 volumes of water. The resulting solution was filtered to remove insolubles and combined with the washings obtained in the washing of the crude 2,6-NDCA. An aqueous 15% sodium carbonate solution was added to the combined solutions in an amount sufficient to increase the pH to 8 and heating was performed for 30 minutes at 60° C. with stirring.

After cooling the solution, the reddish gray precipitates which separated out were collected by filtration and dried to give 171 g of reddish-gray solids. Upon the analysis of the solids, it was found that 97.8% of cobalt, 97.5% of manganese, and 99.1% of cerium based on the amounts of heavy metals used in the oxidation reaction were recovered.

When these recovered heavy metals in the form of carbonates were used as a catalyst to perform oxidation of 2,6-DIPN under the same conditions as above, the yield of the resulting crude 2,6-NDCA was 93.0 mol %. Thus, no substantial loss in yield of 2,6-NDCA was observed when the recovered heavy metal compounds were used as an oxidation catalyst.

EXAMPLE 3

A crude 2,6-NDCA (680 g) obtained by oxidation of 2,6-DIPN in the same manner as described in Example 1 was washed with a mixture of 6800 g of water and 208 g of sulfuric acid at 20° C. by stirring for 1 hour. The slurry was filtered to collect a washed crude 2,6-NDCA.

The washed crude 2,6-NDCA was esterified with methyl alcohol. A Hastelloy autoclave was charged with 433 g of the washed crude 2,6-NDCA, 4330 g of methyl alcohol, and 65 g of 98% sulfuric acid and the mixture was allowed to react for 4 hours at 120° C. At the end of the esterification, the reaction mixture was filtered to collect a crude 2,6-NDCA dimethyl ester.

The crude 2,6-NDCA ester was washed with 5000 ml of water by stirring at room temperature for 30 minutes. After washing, the insolubles were separated by filtration and dried to give 467 g of pale yellow, washed crude 2,6-NDCA ester, which had a purity of 98%.

The washed crude 2,6-NDCA ester was purified by recrystallization and subsequent distillation in the same manner as described in Example 1 to give a purified 2,6-NDCA product.

The product was of a quality similar to that of Example 1. The purity of 2,6-NDCA dimethyl ester in the product was 99.9% plus and it contained 4 ppm of 2,6-NDCA monomethyl ester, at most 20 ppm of naphthoate esters, 0.5 ppm of bromine, and 0.3 ppm of sulfur.

The filtrates obtained from the oxidation and esterification were distilled in the same manner as described in Example 1 and the residues were combined and dissolved in 20 volumes of water. The resulting solution was filtered to remove insolubles and combined with the washings obtained in washing of the crude 2,6-NDCA and crude 2,6-NDCA ester. An aqueous 15% sodium carbonate solution was added to the combined solutions in an amount sufficient to increase the pH to 8 and heating was performed for 30 minutes at 60° C. with stirring.

After cooling the solution, the reddish gray precipitates which separated out were collected by filtration and dried to give 172 g of reddish gray solids. Upon the analysis of the solids, it was found that 98.5% of cobalt, 98.2% of manganese, and 99.2% of cerium based on the amounts of heavy metals used in the oxidation reaction were recovered.

When these recovered heavy metals in the form of carbonates were used as a catalyst to perform oxidation of 2,6-DIPN under the same conditions as above, the yield of the resulting crude 2,6-NDCA was 93.2 mol %. Thus, no substantial loss in yield of 2,6-NDCA was observed when the recovered heavy metal compounds were used as an oxidation catalyst.

EXAMPLE 4

The recovery of heavy metals from the filtrates obtained from the oxidation reaction mixture and the esterification reaction mixture and the washings obtained in washing of the crude 2,6-NDCA ester were carried out in the same manner as described in Example 1 except that an aqueous 15% sodium carbonate solution was added in an amount sufficient to increase the pH to 8 and was stirred for 30 minutes at 25° C. The resulting precipitates were difficult to separate by filtration, and the time required to separate the precipitates by filtration was about 90 times as long as for Example 1.

On the other hand, when the sodium carbonate solution was added in an amount sufficient to increase the pH to 7.2 and stirring was performed at 80° C. for 30 minutes, the solids recovered by filtration weighed about 181 g. Thus, the recovery of heavy metals was remarkably decreased compared to Example 1.

EXAMPLE 5 (COMPARATIVE)

The procedure of Example 1 was repeated except that 600 g of the washed crude 2,6-NDCA ester were recrystallized from 4800 g of methyl alcohol and the resulting recrystallized 2,6-NDCA ester (500 g) was distilled in a distillation column at a reflux ratio of 1. The number of theoretical plates of the distillation column was 7. Under these conditions, the value for $[(B/A)+0.4s+2.9r]$ was calculated to be 13.7 which did not satisfy inequality (1). The distillate was collected in the same manner as described in Example 1.

The product had a purity of 2,6-NDCA dimethyl ester of 99.8% and it contained 590 ppm of 2,6-NDCA monomethyl ester, at most 240 ppm of methyl naphthoate isomers, 113 ppm of bromine, and 84 ppm of sulfur. It had a Hazen number of 100.

When the 2,6-NDCA ester product was copolymerized with ethylene glycol, a slightly colored polyethylene-2,6-naphthalate of a relatively inferior quality was formed.

EXAMPLE 6

Continuous oxidation of 2,6-DIPN was performed. To an titanium-lined autoclave having a capacity of 20 liter, a catalyst solution consisting of cobalt acetate tetrahydrate, manganese acetate tetrahydrate, cerium acetate monohydrate, potassium bromide, potassium acetate, and acetic acid at a weight ratio of 5.48/5.39/7.38/7.85/6.48/230 was fed through a catalyst feeding line at a rate of 2626 g/hr and simultaneously molten 2,6-DIPN was fed through a separate substrate feeding line at a rate of 700 g/hr. The temperature of the catalyst solution was 100° C. and that of the molten 2,6-DIPN was 80° C. The oxidation reaction was continued for 2 hours at a temperature of 200° C. and a pressure of 30 kg/cm$^2$ under stirring while air was passed through the reaction mixture at such a rate that the oxygen concentration of the vented gas was maintained at no greater than 8%. The reaction mixture was continuously withdrawn from the autoclave through a product discharging valve.

The reaction mixture was filtered and the filter cake (crude 2,6-NDCA) was washed with an aqueous 5% sulfuric acid and dried to give a washed crude 2,6-NDCA with a yield of 93.4 mol %. It had a degree of coloration of 2.97 in terms of OD (optical density). The OD was measured by dissolving 1 g of a sample in 9 g of 10% KOH solution and determining the absorbance of the solution in a cell with a light-path length of 1 cm at a wavelength of 500 nm.

The filtrate obtained by filtration of the reaction mixture and the washings obtained by washing of the crude 2,6-NDCA were combined and distilled to remove the solvent and the residue was washed with water to recover polymeric by-products formed in the oxidation reaction. The proportion of the recovered polymeric by-products was 0.4% based on the weight of 2,6-DIPN used.

EXAMPLE 7

Following the procedure described in Example 6, 2,6-DIPN was continuously oxidized with air. In this example, 2,6-DIPN was fed to the reactor through the substrate feeding line in the form of a solution in acetic acid (weight ratio of 2,6-DIPN to acetic acid=75:25) at a rate of 950 g/hr.

The purity of the washed crude 2,6-NDCA was 98.9% and its degree of coloration was OD=2.80. The yield was 93.5 mol %.

The proportion of polymeric by-products recovered in the same manner as described in Example 6 was 0.4% based on the weight of 2,6-DIPN used.

EXAMPLE 8 (COMPARATIVE)

Continuous oxidation of 2,6-DIPN was performed in the same manner as described in Example 6 except that a solution containing both the catalyst and the starting material (substrate) was continuously fed to the reactor. The solution consisted of cobalt acetate tetrahydrate, manganese acetate tetrahydrate, cerium acetate monohydrate, potassium bromide, potassium acetate, 2,6-DIPN, and acetic acid at a weight ratio of 5.48/5.39/7.38/7.85/6.48/70/230. It was fed through the catalyst feeding line at a rate of 3326 g/hr.

The purity of the washed crude 2,6-NDCA was 97.2% and its degree of coloration was OD=greater than 4.0. The yield was 89.2 mol %.

The proportion of polymeric by-products recovered in the same manner as described in Example 6 was 3.8% based on the weight of 2,6-DIPN used.

Although the invention has been described with respect to preferred embodiments, it is to be understood that variations and modifications may be employed without departing from the concept of the invention as defined in the following claims.

What is claimed is:

1. A process for preparing a high-purity naphthalenecarboxylic acid ester comprising the steps of:
    (a) oxidizing a substituted naphthalene with molecular oxygen in the presence of a heavy metal catalyst, an alkali metal compound, and a bromide in a solvent which comprises a lower aliphatic monocarboxylic acid to form a naphthalenecarboxylic acid;
    (b) separating the oxidation product into a crude naphthalenecarboxylic acid and a filtrate;
    (c) optionally washing the crude naphthalenecarboxylic acid with at least one of water, an acid, and an aqueous acid solution to give a washed crude naphthalenecarboxylic acid;
    (d) esterifying the crude or washed crude naphthalenecarboxylic acid in the presence of an esterification catalyst in an alkyl alcohol;
    (e) separating the esterification product into a crude naphthalenecarboxylic acid ester and a filtrate;
    (f) optionally washing the crude naphthalenecarboxylic acid ester with at least one of water, an aqueous acid solution, and an alkyl alcohol to give a washed crude naphthalenecarboxylic acid ester;
    (g) recrystallizing the crude or washed crude naphthalenecarboxylic acid ester from an organic solvent to give a recrystallized naphthalenecarboxylic acid ester; and
    (h) distilling the recrystallized naphthalenecarboxylic acid ester to give a high-purity naphthalenecarboxylic acid ester;
    wherein at least one of the washing steps (c) and (f) is performed.

2. The process of claim 1 which further comprises the steps of:
    (i) treating the filtrates obtained in separating steps (b) and (e) and the washings obtained in washing steps (c) and (f) with a carbonate ion-forming compound in an amount sufficient to precipitate heavy metals present therein as carbonates, and
    (j) recovering the precipitates of heavy metal carbonates for reuse as an oxidation catalyst in step (a).

3. The process of claim 1 wherein the substituted naphthalene used in step (a) has one or more substituents selected from alkyl and acyl groups and oxidation intermediates of these groups.

4. The process of claim 1 wherein the heavy metal catalyst used in step (a) is one or more metal compounds selected from cobalt, manganese, nickel, copper, cerium, iron, and zinc compounds.

5. The process of claim 1 wherein the alkali metal compound used in step (a) is selected from sodium compounds and potassium compounds.

6. The process of claim 1 wherein the oxidation in step (a) is performed continuously by continuously feeding the substituted naphthalene and the heavy metal catalyst separately to a reactor.

7. The process of claim 1 wherein the esterification catalyst used in step (d) is selected from sulfuric acid, hydrochloric acid, phosphoric acid, toluenesulfonic acid, and tetraisopropyl titanate.

8. The process of claim 1 wherein the alkyl alcohol used in steps (d) and (f) is selected from methyl alcohol, ethyl alcohol, propyl alcohols, and butyl alcohols.

9. The process of claim 1 wherein the acid or acid solution used in steps (c) and (f) is a acid selected from sulfuric acid, hydrochloric acid, nitric acid, and acetic acid or its aqueous solution.

10. The process of claim 1 wherein the solvent for recrystallization used in step (g) is selected from alkyl and aralkyl alcohols, alkylbenzenes, aliphatic hydrocarbons, tetrahydrofuran, pyridine, dimethylacetamide, dimethylsulfoxide, dimethylformamide, chloroform, acetone, and ligroin.

11. The process of claim 1 wherein the conditions for recrystallization and distillation in steps (g) and (h) satisfy the following inequality:

$$(B/A)+0.4s+2.9r>14$$

where
   A: weight of NCA ester to be recrystallized (grams),
   B: weight of recrystallization solvent (grams),
   s: number of theoretical plates of distillation column, and
   r: reflux ratio.

12. The process of claim 2 wherein the carbonate ion-forming compound used in step (i) is selected from sodium carbonate, potassium carbonate, ammonium carbonate, sodium bicarbonate, and potassium bicarbonate.

13. The process of claim 2 wherein the treatment with the carbonate ion-forming compound in step (i) is performed at a pH of 7.5 or higher and a temperature of 50° C. or higher.

14. The process of claim 2 which further comprises the step of (k) washing the precipitates of heavy metal carbonates recovered in step (j) with at least one organic solvent selected from alkyl alcohols and ketones.

15. The process of claim 14 wherein the washed precipitates of heavy metal carbonates are recycled to step (a) directly for reuse as an oxidation catalyst.

16. The process of claim 14 wherein the washed precipitates of heavy metal carbonates are reacted with a lower aliphatic carboxylic acid to convert them into heavy metal carboxylates, which are then recycled to step (a) for reuse as an oxidation catalyst.

17. A process for preparing a high-purity naphthalenecarboxylic acid ester comprising the steps of:
    (a) oxidizing a substituted naphthalene with molecular oxygen in the presence of a heavy metal catalyst, an alkali metal compound, and a bromide in a solvent which comprises a lower aliphatic monocarboxylic acid to form a naphthalenecarboxylic acid;
    (b) separating the oxidation product into a crude naphthalenecarboxylic acid and a filtrate;

(c) optionally washing the crude naphthalenecarboxylic acid with at least one of water, an acid, and an aqueous acid solution to give a washed crude naphthalenecarboxylic acid;
(d) esterifying the crude or washed crude naphthalenecarboxylic acid in the presence of an esterification catalyst in an alkyl alcohol;
(e) separating the esterification product into a crude naphthalenecarboxylic acid ester and a filtrate;
(f) optionally washing the crude naphthalenecarboxylic acid ester with at least one of water, an aqueous acid solution, and an alkyl alcohol to give a washed crude naphthalenecarboxylic acid ester;
(g) recrystallizing the crude or washed crude naphthalenecarboxylic acid ester from an organic solvent to give a recrystallized naphthalenecarboxylic acid ester;
(g) distilling the recrystallized naphthalenecarboxylic acid ester to give a high-purity naphthalenecarboxylic acid ester;
(i) treating the filtrates obtained in separating steps (b) and (e) and the washings obtained in washing steps (c) and (f) with a carbonate ion-forming compound in an amount sufficient to precipitate heavy metals present therein as carbonates,
(j) recovering the precipitates of heavy metal carbonates for reuse as an oxidation catalyst in step (a), and
(k) optionally washing the precipitates of heavy metal carbonates recovered in step (j) with at least one organic solvent selected from alkyl alcohols and ketones,
wherein at least one of the washing steps (c) and (f) is performed.

18. A method for purification of a naphthalenecarboxylic acid ester prepared by esterification of a naphthalenecarboxylic acid in an alkyl alcohol in the presence of an esterification catalyst, which comprises washing the naphthalenecarboxylic acid ester with at least one of water, an aqueous acid solution, and an alkyl alcohol and subjecting the washed ester to recrystallization and subsequent distillation under conditions which satisfy the following inequality:

$$(B/A) + 0.4s + 2.9r > 14$$

where
A: weight of NCA ester to be recrystallized (grams),
B: weight of recrystallization solvent (grams),
s: number of theoretical plates of distillation column, and
r: reflux ratio.

19. The method of claim 18 wherein the naphthalenecarboxylic acid is prepared by oxidizing a substituted naphthalene with molecular oxygen in the presence of a heavy metal catalyst, alkali metal compound, and a bromide in a solvent which comprises a lower aliphatic monocarboxylic acid.

20. The method of claim 19 wherein the ratio B/A is at least 3, the value for S is at least 3, and the value for r is at least 0.5

* * * * *